United States Patent
Hood, III

[19]

[11] Patent Number: 6,010,627
[45] Date of Patent: Jan. 4, 2000

[54] DEVICE FOR CONCENTRATING PLASMA

[75] Inventor: Andrew G. Hood, III, Redwood City, Calif.

[73] Assignee: Quantic Biomedical Partners, Redwood City, Calif.

[21] Appl. No.: 08/668,075

[22] Filed: Jun. 19, 1996

Related U.S. Application Data

[63] Continuation-in-part of application No. 08/481,239, Jun. 6, 1995, abandoned.

[30] Foreign Application Priority Data

Jun. 5, 1996 [WO] WIPO ................ PCT/US96/08289

[51] Int. Cl.$^7$ ........................... B01D 61/18; B01D 63/02
[52] U.S. Cl. ............................ 210/321.6; 210/321.78; 210/321.79; 210/321.8; 210/321.87; 210/321.88; 210/321.89; 210/416.1; 210/433.1; 436/178
[58] Field of Search ................................ 210/650, 651, 210/321.6, 321.78, 321.79, 321.8, 321.87, 321.88, 321.89, 416.1, 433.1, 435, 497.01, 500.23; 422/99, 101, 102; 436/177, 178; 604/187

[56] References Cited

U.S. PATENT DOCUMENTS

| | | | |
|---|---|---|---|
| 4,004,975 | 1/1977 | Lionetti et al. | 195/1.8 |
| 4,159,896 | 7/1979 | Levine et al. | 23/230 B |
| 4,343,793 | 8/1982 | Wissler | 424/101 |
| 4,359,049 | 11/1982 | Redl et al. | 604/82 |
| 4,362,567 | 12/1982 | Schwarz et al. | 106/157 |

(List continued on next page.)

FOREIGN PATENT DOCUMENTS

| | | |
|---|---|---|
| 0076665A3 | 4/1983 | European Pat. Off. . |
| 0112094A1 | 6/1984 | European Pat. Off. . |
| 0399083A1 | 11/1990 | European Pat. Off. . |
| 0446713A2 | 9/1991 | European Pat. Off. . |
| 2 515965 | 5/1983 | France . |
| 60-011166 | 1/1985 | Japan . |
| 6-269497 | 9/1994 | Japan . |
| WO 84/00892 | 3/1984 | WIPO . |
| WO 86/03122 | 6/1986 | WIPO . |
| WO 88/02259 | 4/1988 | WIPO . |
| WO 91/00046 | 1/1991 | WIPO . |
| WO 91/09573 | 7/1991 | WIPO . |

OTHER PUBLICATIONS

Amicon technical data sheet, entitled "Minifilter Plus™ for pediatric patients, Minifilter® hemofilter for neonatal patients for Continuous Arteriovenous Renal Replacement Therapy for Neonatal and Pediatric Patients" (undated).

Bertolini, F. et al., "Platelet Concentrates Stored in Synthetic Medium after Filtration", 62 *Vox Sang* 82–86 (1992).

Bloom, A., "Physiology of Blood Coagulation", 20 *Haemostasis* 14–29 (1990).

Boyd, R., et al., *Basic Medical Microbiology* (3rd ed.) 324–325 (Little, Brown and Co. 1986).

Hartman, A. R. et al., "Autologous Whole Plasma Fibrin Gel; Intraoperative Procurement", *Arch. Surg.* 127:357–359 (1992).

Hjortdal, V. et al., "Venous Ischemia in Skin Flaps: Microcirculatory Intravascular Thrombosis", 93 *Plastic and Reconstructive Surgery* 366–374 (1994).

(List continued on next page.)

*Primary Examiner*—John Kim
*Attorney, Agent, or Firm*—McCutchen, Doyle, Brown & Enersen, LLP; Emily M. Haliday

[57] ABSTRACT

The present invention provides a device for concentrating a blood fraction. The device includes an ultrafiltration unit connected to a fluid delivery system for delivering the blood fraction to be concentrated into the ultrafiltration unit. The device also includes a purge fluid delivery system for expelling concentrate from the ultrafiltration unit. In one embodiment, the device accommodates multiple cycles of concentration. A blood fraction concentration method is also provided. The device and method of the present invention are particularly useful for preparing a plasma concentrate suitable for use in a coagulum-based wound sealant.

7 Claims, 3 Drawing Sheets

U.S. PATENT DOCUMENTS

| | | |
|---|---|---|
| 4,427,650 | 1/1984 | Stroetmann .................................. 424/46 |
| 4,627,879 | 12/1986 | Rose et al. ................................. 106/124 |
| 4,680,025 | 7/1987 | Kruger et al. ................................. 604/6 |
| 4,696,748 | 9/1987 | Nitadori et al. ...................... 210/500.23 |
| 4,735,616 | 4/1988 | Eibl et al. .................................. 604/191 |
| 4,800,022 | 1/1989 | Leonard ..................................... 210/652 |
| 4,978,336 | 12/1990 | Capozzi et al. ............................. 604/82 |
| 5,039,401 | 8/1991 | Columbus et al. ....................... 210/117 |
| 5,185,001 | 2/1993 | Galanakis .................................... 604/5 |
| 5,290,552 | 3/1994 | Sierra et al. .......................... 424/94.64 |
| 5,304,372 | 4/1994 | Michalski et al. .................... 424/94.64 |
| 5,318,782 | 6/1994 | Weis-Fogh ................................ 424/529 |
| 5,330,974 | 7/1994 | Pines et al. .................................. 514/21 |
| 5,405,607 | 4/1995 | Epstein .................................. 424/94.64 |
| 5,428,008 | 6/1995 | Chao et al. ................................... 514/8 |
| 5,437,598 | 8/1995 | Antwiler ....................................... 494/1 |
| 5,464,535 | 11/1995 | Shettigar ............................. 210/321.89 |
| 5,585,007 | 12/1996 | Antanavich .............................. 210/782 |
| 5,601,727 | 2/1997 | Bormann et al. ........................ 210/651 |
| 5,674,394 | 10/1997 | Whitmore ............................ 210/321.8 |

OTHER PUBLICATIONS

Hood, A. G. et al., "Perioperative Autologous Sequestration III: A New Physiologic Glue with Wound Healing Properties", *Trans. Am. Acad. Cardiovasc. Perf.* 14:126–129 (1993).

Keating, R. F. et al., "Tethered Cord Dural Repair With Intraoperative Autologous Fibrin Glue", Presented at American Assn. of Neurological Surgeons Pediatric Session, Vancouver, Canada, Dec., 1992.

Koerner, K. et al., "Quality of pooled platelet concentrates prepared from buffy coats and stored in an additive solution after filtration", 70 *Ann Hematol*. 97–102 (1995).

Minntech Corporation product brochure, entitled "Instructions for Use Minntech Hemocor HPH™ Hemoconcentrator" (undated).

Moretz, W. H., Jr. et al., "A simple autologous fibrinogen glue for otologic surgery", *Otolaryngology Head and Neck Surg*. 95:122–124 (1986).

Oz, M. C. et al., "Autologous Fibrin Glue From Intraoperatively Collected Platelet Rich Plasma", *Ann. Thorac. Surg*. 53:530–531 (1992).

Quigley, R. L. et al., "Intraoperative Procurement of Autologous Fibrin Glue", *Ann. Thorac. Surg*. 56:387–389 (1993).

Reeder, G. D. et al., "Perioperative Autologous Sequestration I: Physiology, Phenomena and Art", *Trans. Am. Acad. Cardiovasc. Perf*. 14:118–121 (1993).

Reeder, G. D. et al., "Autologous Platelet Gel: An Autologous Method for Improved Wound Closure and Accelerated Healing", Poster Session, Fibrin Sealant: Characteristics and Clinical Uses Conference, Bethesda, Maryland, Dec., 1994.

Sierra, D. H., "Fibrin Sealant Adhesive Systems: A Review of Their Chemistry, Material Properties and Clinical Applications", *J. Biomat. App*. 7:309–352 (1993).

Silver, F. et al., "Preparation and use of fibrin glue in surgery", 16 *Biomaterials* 891–903 (1995).

DEVICE FOR CONCENTRATING PLASMA

CROSS REFERENCE TO RELATED APPLICATIONS

This application is a continuation-in-part of U.S. patent application Ser. No. 08/481,239, filed Jun. 6, 1995, now abandoned.

BACKGROUND OF THE INVENTION

1. Field of the Invention

The present invention relates to a device and method for concentrating a blood fraction. In particular, the device and method are useful for preparing a plasma concentrate for use in a coagulum-based wound sealant.

2. Description of the Related Art

Wound sealants are compositions that mimic the body's natural repair processes when applied to damaged tissues and vessels. In particular, wound sealants are designed to prevent persistent fluid loss from or into a wound, which can increase patient discomfort and morbidity, prolong recovery, and compromise or prevent an otherwise successful surgical outcome.

The problem of fluid leakage is particularly severe in highly vascularized tissues, such as kidney, liver, spleen and cancellous bone, which continue to bleed even after electrocautery. Arterial vascular grafts often leak at sites of anastomosis, along suture lines, and even through the grafts. Dural wounds are extremely difficult to repair, with a 30 percent failure rate for some of the best currently available procedures. Resection of lung tissue often results in persistent air leaks, which significantly prolong recovery. Moreover, such problems are often exacerbated in patients suffering from diabetes or other disease processes that impair normal wound healing.

The use of fibrinogen-based wound sealants has received widespread attention as a solution to the problem of fluid leakage. Such wound sealants are formed by using a fibrinogen activator, such as thrombin, to cleave fibrinogen to form fibrin, followed by formation of a coagulum by fibrin-fibrin crosslinking. Fibrin molecules also form crosslinks with collagen, a principle constituent of most tissues. These fibrin-collagen crosslinks promote adherence of the coagulum to the tissue to be sealed.

This approach offers a number of advantages. First, the rate of coagulum formation can be adjusted to suit the needs of a particular application by adjusting the concentration of fibrinogen activator in the mixture. Second, fibrinogen-based wound sealants are predominantly physiologic in origin, and therefore normal fibrinolytic processes remove the coagulum, typically within two to three weeks, leaving minimal scarring. If desirable, coagulum breakdown can be slowed by the addition of antifibrinolytics such as $\epsilon$-amino caproic acid, tranexamic acid, or aprotinin. Finally, other chemical agents, such as antibiotics or anticancer drugs, can be added to the fibrinogen and/or fibrinogen activator solutions before mixing to provide sustained release of the agent at the wound site.

Fibrin for these wound sealants is typically obtained from blood or a blood fraction, such as plasma. One type of wound sealant which depends on fibrinogen and other associated plasma proteins as the procoagulant constituents has been termed "fibrin glue". Wound sealants of this type, derived from pooled blood, are widely available in Europe. However, the sale of such pooled blood-derived fibrin glues is banned in the United States because of the risk of disease transmission. Recent efforts aimed at avoiding the problems of disease transmission and immunological complications associated with the use of donor materials, have focused on the possibility of using a patient's own plasma as a fibrinogen source. However, the strength and adhesiveness of fibrinogen-based wound sealants are directly related to the fibrinogen concentration. Typical plasma fibrinogen values, which range from 2.0 to 4.5 for healthy patients, are known to provide too low a fibrinogen concentration to form a suitable fibrinogen-based wound sealant. Furthermore, disease processes, drugs, and treatment regimens can cause plasma fibrinogen levels to drop significantly lower than normal values.

Consequently, various methods of concentrating autologous fibrinogen-containing solutions have been explored. Cryoprecipitation methods are effective, but entail complex processing steps and require expensive equipment and highly trained personnel. Furthermore, preparation time ranges from hours to days, which rules out the use of cryoprecipitation methods when unexpected, acute treatment is required. Platelet-rich plasma has been used to provide clotting factors present in platelets. This use has frequently been unsuccessful because the fibrinogen level of platelet-rich plasma remains low. Other methods are based on admixture of foreign materials, such as polyethylene glycol or ammonium sulfate. These methods also suffer from excessive complexity and can expose the patient to undesirable contaminants.

A reliable method of preparing a plasma concentrate containing fibrinogen that is rapid, simple, and economical would facilitate the preparation of coagulum-based wound sealants. In particular, the ability to rapidly prepare autologous wound sealants would make the benefits of wound sealants available to patients who require acute treatment.

SUMMARY OF THE INVENTION

The present invention provides a device for concentrating a blood fraction. The device includes an ultrafiltration unit having first and second openings and an outlet adapted to connect to a vacuum source. The first opening is connected by a first valve to a fluid delivery system for delivering the blood fraction to be concentrated into the ultrafiltration unit. The second opening is connected by a second valve to a purge fluid delivery system for expelling concentrate from the ultrafiltration unit. In one embodiment, the device accommodates multiple cycles of concentration.

A blood fraction concentration method is also provided. One embodiment of the method provides single-cycle concentration, while another embodiment facilitates multi-cycle processing. The device and method of the present invention are particularly useful for preparing a plasma concentrate suitable for use in a coagulum-based wound sealant.

DETAILED DESCRIPTION OF THE INVENTION

Figure 1:
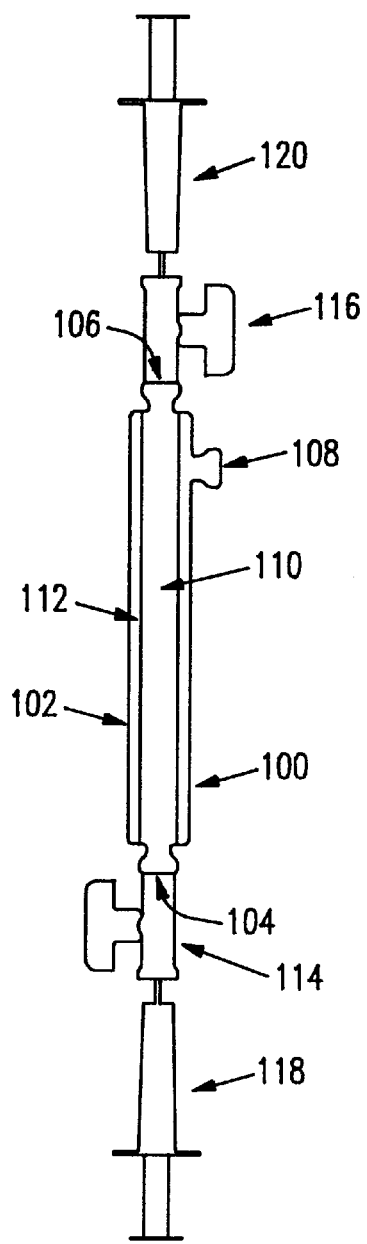
FIG. 1 is a side view of a concentration device according the present invention, wherein the device has a fluid delivery system, an ultrafiltration unit, and a purge fluid delivery system.

The present invention provides a device and method for concentrating a blood fraction. In particular, the concentrator is useful for concentrating a blood fraction, typically plasma, to provide a concentration of blood procoagulants suitable for use in preparing coagulum-based wound sealants. In the device and method of the present invention, concentration is achieved by the process of ultrafiltration.

Ultrafiltration combines the use of pressure and semi-permeable membranes to separate molecular species by size, shape, and/or charge. In general, a solution in contact with a semi-permeable membrane is subjected to a pressure differential across the membrane, which results in the flux of particular species through the membrane into the "filtrate". Any species that are unable to pass through the membrane are said to be "retained". Standard applications for ultrafiltration have included solute recovery, salt removal, buffer exchange, and purification.

In hematology, ultrafiltration has been put to numerous well known uses. Generally, ultrafiltration has been used in hemodialysis to filter blood of patients with absent or impaired kidney function or to remove poisons such as toxic doses of aspirin or narcotics from the bloodstream of patients. Ultrafiltration has also been used for hemoconcentration to remove water and small molecules, generally less than 65,000 daltons (D), from whole blood. The present invention provides a concentrator that includes an ultrafiltration unit suitable for use with blood or blood fractions such as plasma.

The ultrafiltration unit is in fluid communication with a first syringe or other fluid delivery system through a first valve to deliver a blood fraction to the ultrafiltration unit. The concentrator also includes a second syringe or other fluid delivery system for expelling concentrate from the ultrafiltration unit, which syringe is connected to the ultrafiltration unit through a second valve.

In one embodiment, concentrate is expelled into the first syringe. In another embodiment, concentrate is expelled into a third syringe or other fluid receptacle connected to the first valve. This embodiment is particularly useful when the blood fraction contains undesirable elements that cannot be removed by ultrafiltration, such as, for example, red blood cells or when multiple concentrates are produced in sequential cycles of concentration.

The present invention additionally provides a method for concentrating a blood fraction. One embodiment provides a single cycle of concentration, while another embodiment facilitates multi-cycle processing. Variations of each of these embodiments allow processing of whole blood, as described hereinafter.

The concentrator and method of the present invention are described in detail below with reference to processing of plasma to produce a concentrate having a fibrinogen concentration suitable for coagulum-based wound sealants. Although the following description relates to increasing the concentration of fibrinogen and other procoagulant proteins, cellular components of whole blood such as platelets, white cells, or buffy coat can be included in the blood fraction and are also concentrated using the device and method of this invention. The following description is intended as illustrative and should not be taken as limiting. From the teachings herein, those skilled in the art can readily determine modifications of the disclosed device and method that allow the preparation of other types of blood fraction concentrates.

Referring to FIG. 1, the concentrator includes ultrafiltration unit 100. Ultrafiltration devices for use in hematologic applications are well known and are commercially available from numerous sources. Ultrafiltration unit 100 includes housing 102 having a first and a second opening, openings 104 and 106, respectively at opposite ends of ultrafiltration unit 100 and outlet 108 between openings 104 and 106. Typically, outlet 108 is closer to opening 106 than to opening 104. In one embodiment, outlet 108 is located at a distance from opening 106 that is about a fifth of the length of housing 102. The location of the outlet is of no consequence for the purposes of this invention. In addition, ultrafiltration unit 100 is shown with one outlet. Typically, however, ultrafiltration units used in hematology have two outlets. Both outlets are used for hemodialysis. However, one outlet is capped for use in hemoconcentration (also known as hemofiltration). Commercial ultrafiltration units are sold with caps for sealing the outlets, and only one outlet is required for purposes of this invention.

Outlet 108 is adapted to connect to a vacuum source via a conventional connector. For example, in FIG. 1, outlet 108 has a flange that can frictionally engage vacuum tubing or that can engage an appropriately designed adaptor. However, if a pressure differential across the semi-permeable membrane is achieved by exerting pressure on the blood fraction in the concentrate chamber, outlet 108 can be connected to a fluid receptacle that receives the filtrate.

Ultrafiltration unit 100 includes a semi-permeable membrane oriented in housing 102 to define two chambers, concentrate chamber 110 and filtrate chamber 112. The inner chamber for concentrate (concentrate chamber 110) on the inside of the semi-permeable membrane communicates with openings 104 and 106, defining a flowpath for fluid between openings 104 and 106 such that fluid entering ultrafiltration unit 100 through either of openings 104 and 106 flows through the concentrate chamber to the other opening or through the semi-permeable membrane into the filtrate chamber 112. The semi-permeable membrane together with housing 102 also define an outer chamber for filtrate (filtrate chamber 112) between the semi-permeable membrane and housing 102 that communicates with outlet 108. In use, the blood fraction to be concentrated is introduced into concentrate chamber 110, a pressure differential across the semi-permeable membrane is achieved by vacuum applied to outlet 108, and plasma components able to cross the membrane move from concentrate chamber 110 into filtrate chamber 112. Alternatively, pressure can be applied to openings 104 and 106 to create a pressure differential across the semi-permeable membrane.

Although the semi-permeable membrane in FIG. 1 is a single membrane within the housing, other membrane configurations are suitable, including, for example, a parallel plate configuration, which corresponds to a flat sheet with a series of folds. The parallel plate ultrafiltration units that are commercially available typically have priming volumes in the range of 75 to 100 ml, and thus are useful for relatively large-scale processes. Other suitable configurations of ultrafiltration units can be used. For example, the outer chamber can be used as the concentrate chamber and the inner chamber can be used as the filtrate chamber for any of the ultrafiltration units. In such configurations, the vacuum would be connected to the ends of the housing where the fluid delivery systems are located in FIG. 1, and the fluid delivery systems would be attached to the outlet that communicate with the outer chamber. Additional configurations will be readily apparent to those of skill in the art.

The semi-permeable membrane has a molecular weight cut-off suitable for retaining one or more desired species. Because retention is influenced by a variety of additional factors (such as molecular shape and charge), the membrane is typically selected to retain species having molecular weights at least about 100% below the molecular weight of the smallest desired species. In general, using a membrane with the highest molecular weight cut-off that retains the desired species is advantageous, as processing time increases with decreasing molecular weight cut-off. However, membranes with lower molecular weight cut-offs than required can be used.

The degree of retention of species of a particular molecular weight can be expressed as the "sieving coefficient" of the membrane. The sieving coefficient for a given solute is the concentration of solute in the ultrafiltrate divided by the concentration of solute in the concentrate. Thus, the smaller the sieving coefficient for solutes of a particular molecular weight, the greater the retention of such solutes in the concentrate. A membrane with a sieving coefficient of 0.10 or less (i.e., 90% or greater retention) at the molecular weight cut-off generally provides suitable results.

In preparing a plasma concentrate for a coagulum-based wound sealants, the primary species to be concentrated is the protein fibrinogen, which has a molecular weight of 330,000 to 340,000 D. However, it is advantageous to retain various clotting factors such as Factor V (55,000 to 60,000 D) and Factor X (55,000 to 60,000 D), as well as other desirable constituents, including growth factors such as platelet-derived growth factor (30,000–35,000 D). For this application, therefore, a semi-permeable membrane with a sieving coefficient of about 0.05 or less at 30,000 D molecular weight provides good results.

The semi-permeable membrane should resist breakdown at the pressures and temperatures encountered in the particular application. Commercially available polysulfone hollow fiber membranes can be employed at pressure differentials of up to about 500 mm Hg and at temperatures ranging from around 4° C. to about 50° C.

The concentrator of the present invention also includes two valves, shown as stopcocks 114 and 116 in FIG. 1, one connected to each opening. Each stopcock has an open position in which a flowpath through each of the stopcocks communicates with concentrate chamber 110. Commercially available ultrafiltration units have manifolds designed to connect to tubing having an internal diameter of 3/16 or 1/4 inch, depending on the device. The tubing can be connected to the stopcocks by conventional means. For example, the stopcock (commercially available from a number of sources including Medex, Inc.) is fitted with a male luer lock to 1/4" tubing adapter (commercially available from sources such as Minntech Corp. of Minneapolis, Minn.), which in turn is fitted with a piece of 1/4" PVC tubing (about 2 to about 3 cm in length). A hemoconcentrator (commercially available from a number of sources including Minntech Corp., Amicon Corp., and others) is then connected at its inlet to the 1/4" tubing.

Fluid delivery syringe 118 or other fluid delivery system is removably connected to stopcock 114 to form a positive connection during use. Other suitable fluid delivery systems are those capable of ejecting fluid and are well known, such as, for example, a fluid transfer bag (commercially available from Terumo Corp., Tokyo, Japan, and others). Such systems are capable of positively connecting to stopcock 114. When a syringe is used for fluid delivery, stopcock 114 can include, for example, luer lock ears that engage a luer lock fitting on the syringe to form an interlocking connection with the syringe.

The flowpath through stopcock 114 communicates with an interior chamber of fluid delivery syringe 118 and with concentrate chamber 110. In this embodiment, the fluid delivery system need not be capable of injecting fluid into concentrate chamber 110 because the application of vacuum at outlet 108 aspirates fluid in the fluid delivery system into concentrate chamber 110.

Purge fluid syringe 120 or another fluid delivery system is connected to stopcock 116 so that a flowpath formed through stopcock 116 when the stopcock 114 is in an open position communicates with the interior of purge fluid syringe 120 and with concentrate chamber 110. Although FIG. 1 includes purge fluid syringe 120, any system capable of injecting a sufficient amount of fluid to expel fluid from concentrate chamber 110 can be employed. For example, the fluid delivery system can include tubing connected to a pressurized fluid source. In one embodiment, the fluid delivery system is capable of delivering a volume of fluid equal to the priming volume of ultrafiltration unit 100 to purge fluid in concentrate chamber 110.

The surfaces of the concentrator that contact the blood fraction and/or the resulting concentrate should be inert to the blood fraction components and should not substantially denature proteins. In some embodiments, for example, where it is desirable to include cells such as platelets or leukocytes in the blood fraction, the contact surfaces are substantially noncytotoxic. Suitable materials include polycarbonates, polyurethane, acrylics, ABS polymers, polysolfone, and the like.

In embodiments where the sterility of the blood fraction or other liquid composition must be maintained, as in the preparation of a plasma concentrate for a wound sealant, any concentrator surface that contacts the liquid composition and/or the concentrate must be sterile or readily sterilizable. Commercially available ultrafiltration units can be sterilized by treating with agents such as ethylene oxide, formalin, hydrogen peroxide, or sodium hypochlorite. Sterile ultrafiltration units are commercially available for hematologic uses. Syringes and other fluid delivery systems are generally commercially available in sterile form as are various valves and stopcocks that are designed to attach to syringes and other blood processing products. The present invention provides a concentration method that is useful for single-cycle concentration of a blood fraction. One embodiment of this method is illustrated herein by the use of a concentrator such as that shown in FIG. 1 to produce a plasma concentrate suitable for use in a wound sealant. In this embodiment, the blood fraction to be concentrated is a procoagulant-containing fraction of anticoagulated whole blood prepared by standard techniques. The blood is anticoagulated at the time of withdrawal, generally using a citrate-based anticoagulant. Any citrate-based anticoagulant is suitable. Standard donor blood collection bags contain citrate-based anticoagulants. For example, those made by Terumo Corporation (Teruflex, CPDA-1) contain 63 ml of citrate phosphate dextrose adenine anticoagulant for collection of 450 ml of blood. Each 63 ml of anticoagulant contains 206 mg citric acid (hydrous) USP, 1.66 g sodium citrate (hydrous) USP, 140 mg monobasic sodium phosphate (hydrous) USP, 1.83 g dextrose (anhydrous) USP and 17.3 g adenine.

Prior to processing, typically whole blood is fractionated to remove most or all of the red blood cells. However, variations of the device and method are described below that facilitate processing whole blood or blood fractions that contain substantial amounts of residual red blood cells. If desired, the blood fraction can be a mixture of plasma with buffy coat obtained from anticoagulated whole blood by a conventional centrifugation process. Other procoagulant-containing blood fractions such as platelet-rich plasma or platelet-poor plasma can also be used. In addition to anti-coagulation agents, buffers, preservatives, or other components can be added to the blood fraction to facilitate processing and/or storage before or after concentration.

Referring to FIG. 1, the blood fraction is introduced into fluid delivery syringe 118, which is connected to stopcock 114. Stopcocks 114 and 116 are initially closed. Purge fluid syringe 120 contains a sterile, physiological solution used to purge concentrate from ultrafiltration unit 100. Any sterile, physiological solution can be used as the purge fluid. For example, physiologic saline, albumin solution (Baxter Travenol, Springfield, Ill.), and the like are suitable. To minimize dilution of fibrinogen in the concentrate, a blood fraction such as plasma can be used as the purge fluid.

To begin the concentration process, a vacuum is applied to outlet 108 by connecting outlet 108 to a vacuum source, such as a vacuum pump. Vacuum levels are limited by the burst capacity of the semipermeable membrane, which can typically withstand a vacuum of about −500 mm Hg (−500 torr). If necessary, the vacuum can be reduced and processing time increased proportionately. Stopcock 114 is switched to the open position, providing a flowpath between fluid delivery syringe 118 and concentrate chamber 110. As a result, the blood fraction in fluid delivery syringe 118 is aspirated into concentrate chamber 110 and fluid is drawn across the membrane and into filtrate chamber 112. The vacuum is removed when the blood fraction has reached the desired degree of concentration, which is typically about three-fold in the case of a plasma concentrate for a wound sealant.

Stopcock 116 is then switched to the open position, providing a flowpath between purge fluid syringe 120 and concentrate chamber 110. Purge fluid is forced through stopcock 116, in this embodiment, by depressing the plunger of purge fluid syringe 120. This forces the concentrate in concentrate chamber 110 to flow through stopcock 114. In this embodiment, concentrate is collected by allowing back-flow through stopcock 114 into fluid delivery syringe 118. To maximize concentrate recovery and minimize dilution, the volume of purge fluid injected into the ultrafiltration unit can be equal to the unit's priming volume.

Figure 2A:
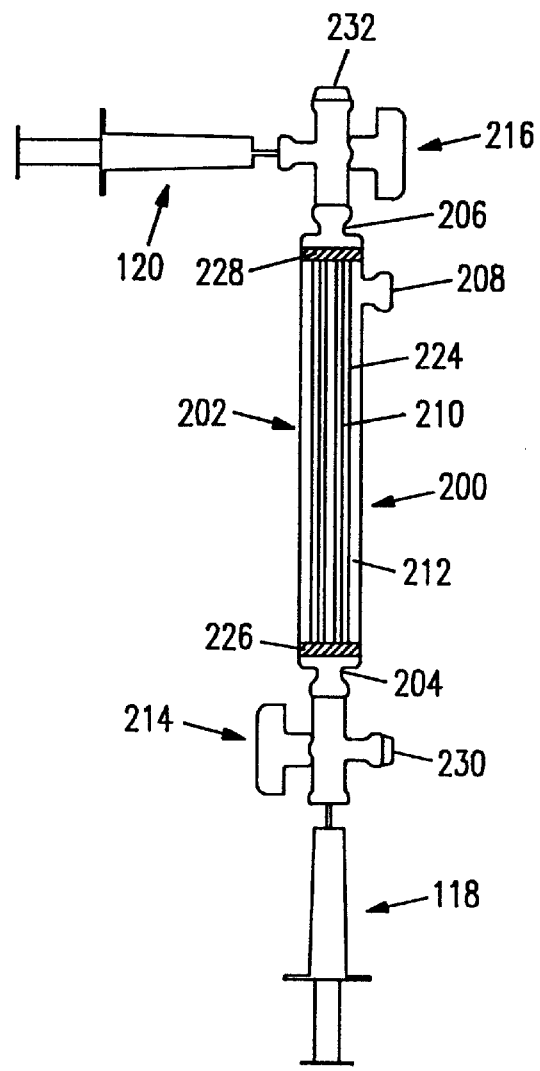
FIG. 2A is a side view of a device similar to that shown in FIG. 1 except that the valves of FIG. 1 have been replaced by tridirectional valves.

Referring to FIG. 2A, ultrafiltration unit 200 is a standard hollow fiber cartridge such as is commercially available from a number of sources including Minntech Corp., Amicon Corp., and others. Ultrafiltration unit 200 is substantially similar to ultrafiltration unit 100 of FIG. 1. Ultrafiltration unit 200 includes housing 202 having first and second manifolds, manifolds 204 and 206, respectively at opposite ends of ultrafiltration unit 100 and outlet 208 between manifolds 204 and 206. Outlet 208 does not differ from outlet 108 in FIG. 1. Manifolds 204 and 206 are substantially similar to openings 104 and 106 in FIG. 1, except that the manifolds form a flowpath to a plurality of hollow fibers, fiber bundle 224 that constitute the semi-permeable membrane. These fibers typically have a lumen diameter on the order of 150 $\mu$M and a wall thickness of about 15 to 25 $\mu$M. Fiber bundle 224 is sealed on each end with a potting material, such as polyurethane, to form seals 226 and 228. The potting material is cut after sealing to form a header that exposes the lumens of the hollow fibers and fiber bundle 224 is encased in housing 202 to form manifolds 204 and 206. Manifolds 204 and 206 are adapted to direct fluid flow to or from the hollow fiber lumens. The lumens, collectively, make up concentrate chamber 210, and filtrate chamber 212 is an annular space between fiber bundle 224 and housing 202. The volume of concentrate chamber 210 is termed the "priming volume" and, in commercially available units, generally ranges from 10 to 50 cc.

Figure 2B:
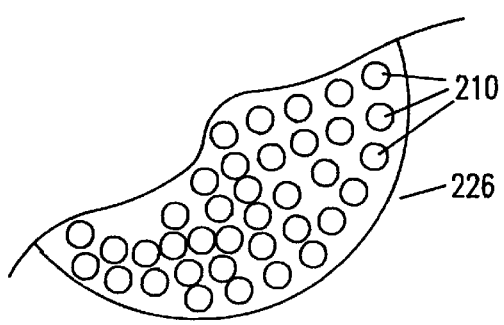
FIG. 2B is a cut away top view of a portion of the ultrafiltration unit of FIG. 2A, illustrating the concentrate chamber of the unit.

Referring to FIG. 2B, a cut away top view of a portion of seal 226 of ultrafiltration unit 100 of FIG. 2A, illustrating the location of concentrate chamber 210 of the unit.

In FIG. 2A, stopcocks 214 and 216 are tridirectional valves illustrated as three-way stopcocks. Fluid delivery syringe 118 is removably connected to stopcock 214, and purge fluid syringe 120 is removably connected to stopcock 216. In this embodiment, only two ports are required per stopcock, and the extra ports are capped with deadender caps 230 and 232. Ultrafiltration unit 200 is used in the same manner as described above for ultrafiltration unit 100 of FIG. 1.

Figure 3:
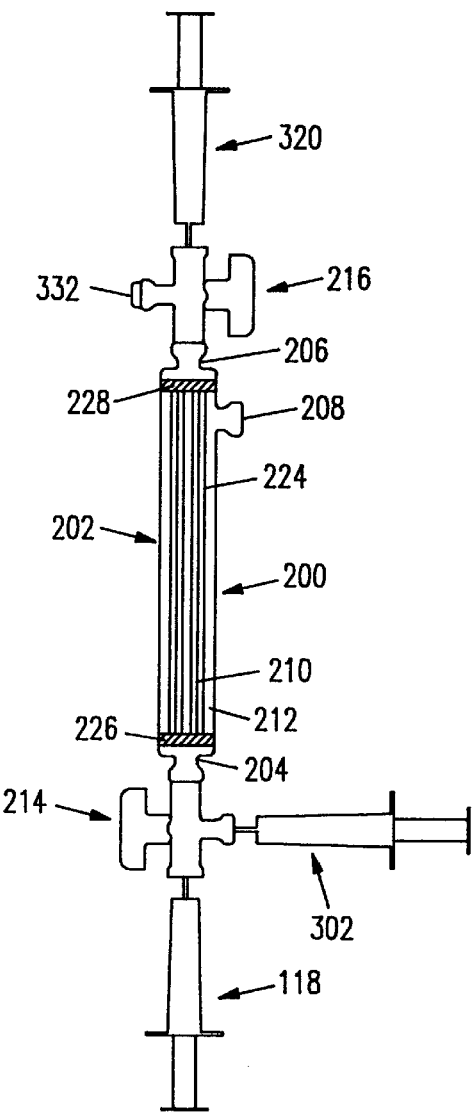
FIG. 3 is a side view of a device similar to that shown in FIG. 2 that includes a fluid receptacle.

FIG. 3 shows a variation of the embodiment depicted in FIG. 2A. In FIG. 3, the positions of purge fluid syringe 320 and deadender cap 332 connected to stopcock 216 are reversed. Thus, the long axis of purge fluid syringe 320 is aligned with that of ultrafiltration unit 200. Those skilled in the art will recognize that the positions of purge fluid syringe 120 and deadender cap 232 in FIG. 2A can also be reversed.

FIG. 3 also differs from FIG. 2A in that the concentrator of FIG. 3 includes a fluid receptacle such as receptacle syringe 302 connected to stopcock 214. The fluid receptacle is shown as a syringe, but can be any fluid receptacle capable of connecting to stopcock 214, including, for example, a fluid transfer bag. In this embodiment, stopcock 214 is a tridirectional valve, e.g. a three way stopcock, that has a second open position to provide a second flowpath. The second flowpath communicates with an interior chamber of receptacle syringe 302 and with concentrate chamber 210. With respect to syringes 118 and 302, the positions of these two assemblies is noncritical, unless the liquid composition contains red blood cells or other undesirable components that are denser than plasma. If such components are present, fluid delivery syringe 118 is oriented so that the undesirable components can settle in a portion of the syringe sufficiently distant from stopcock 214 to prevent egress of the components through the stopcock during processing, as described hereinafter.

As stated above, commercially available hollow fiber ultrafiltration units having a priming volume of from about 10 cc to about 50 cc. When such units are used to concentrate plasma or another blood fraction, the degree of concentration that can be achieved is as high as three-fold. Thus, the present invention facilitates processing of between about 30 to about 150 cc of plasma in one cycle of operation using commercially available ultrafiltration units. These units can be scaled up or down to allow single-cycle processing of larger or smaller volumes, as desired.

In a variation of the above-described concentration method, a device such as that illustrated in FIG. 3 can be used to prepare a concentrate when the liquid composition in fluid delivery syringe 118 contains red blood cells and/or other undesirable components that are sufficiently dense to settle to the bottom of the syringe. In this embodiment, fluid delivery syringe 118 is oriented so that red blood cells can settle on a surface distant, typically at the opposite end of the syringe from stopcock 214. Stopcock 214 is opened to aspirate the portion of the fluid composition that does not comprise red blood cells and then closed to prevent substantial entry of red blood cells into concentrate chamber 210.

After concentration of the blood fraction, stopcock 214 is switched to a second open position, eliminating the flowpath to fluid delivery syringe 118 and opening the flowpath to receptacle syringe 302. The vacuum is removed and concentrate chamber 210 is purged as described above, which forces concentrate through stopcock 214 and into receptacle syringe 302.

The device shown in FIG. 3 can also be employed in a multi-cycle embodiment of the concentration method. Referring to FIG. 3, the blood fraction is contained in fluid delivery syringe 118. Stopcocks 214 and 216 are initially closed. Purge fluid syringe 320 contains purge fluid.

Concentration is initiated by applying a vacuum to outlet 208, as described above, and switching stopcock 214 to the first open position. The relationship of the pressure differential across the semi-permeable membrane to volume of blood fraction processed (ml/minute) is well known. In particular, the processing volumes increase with increasing pressure differentials then level off at higher pressure differentials. Commercially available hemoconcentration units include graphs showing the relationship in their product literature.

As a result of the pressure differential, the blood fraction in fluid delivery syringe 118 is aspirated into concentrate chamber 210 and fluid is drawn across the membrane and into filtrate chamber 212. Stopcock 214 remains in the first open position and additional volumes of blood fraction are drawn into concentrate chamber 210 from fluid delivery syringe 118 as the blood fraction in the chamber is concentrated.

This injection of an additional volume of liquid composition can be accomplished in a variety of ways. If the fluid delivery system is a syringe, the syringe can be removed and refilled after the first volume of liquid composition has been aspirated into concentrate chamber 210. Alternatively, the syringe can be large enough to contain the entire volume of liquid composition to be concentrated. In either case, the additional volume of liquid composition is injected into concentrate chamber 210 by depressing the syringe plunger. Other types of fluid delivery assemblies can be employed, including, for example, assemblies comprising tubing connected to a pressurized fluid source and a push-button type valve that activates flow or a control unit that injects a selected volume of fluid composition at appropriate time intervals.

The injection of an additional volume of blood fraction into concentrate chamber 210 can be used to force the concentrate in the chamber through open stopcock 216 and into receptacle syringe 320. To maximize efficiency, the additional volume can be equal to the priming volume of the concentrator. After all of the concentrate from this processing cycle has been collected, stopcock 216 is closed, and the additional volume of blood fraction is concentrated. If necessary, additional concentration cycles can be carried out by repeating the steps of opening stopcock 216, injecting additional blood fraction through stopcock 214 which forces concentrate in concentrate chamber 210 into receptacle syringe 320, and closing stopcock 216 after the concentrate enters the interior chamber of receptacle syringe 320.

When the last volume of blood fraction has been concentrated, the vacuum is removed, and stopcock 214 is switched to the second open position, opening the flowpath between purge fluid syringe 302 and concentrate chamber 210. Purge fluid is forced through stopcock 214, in this embodiment, by depressing the plunger of purge fluid syringe 302. This forces the last volume of concentrate in concentrate chamber 210 to flow through stopcock 216 and into receptacle syringe 320. Concentrate recovery is maximal when the volume of purge fluid injected into the ultrafiltration unit is equal to the unit's priming volume.

In another embodiment, a concentrator similar to that shown in FIG. 3 can be used to perform multiple cycles of concentration using purge fluid syringe 302 as the fluid receptacle to receive concentrate. Receptacle syringe 320 is used for purge fluid, so that the functions of the syringes are reversed.

Figure 4:
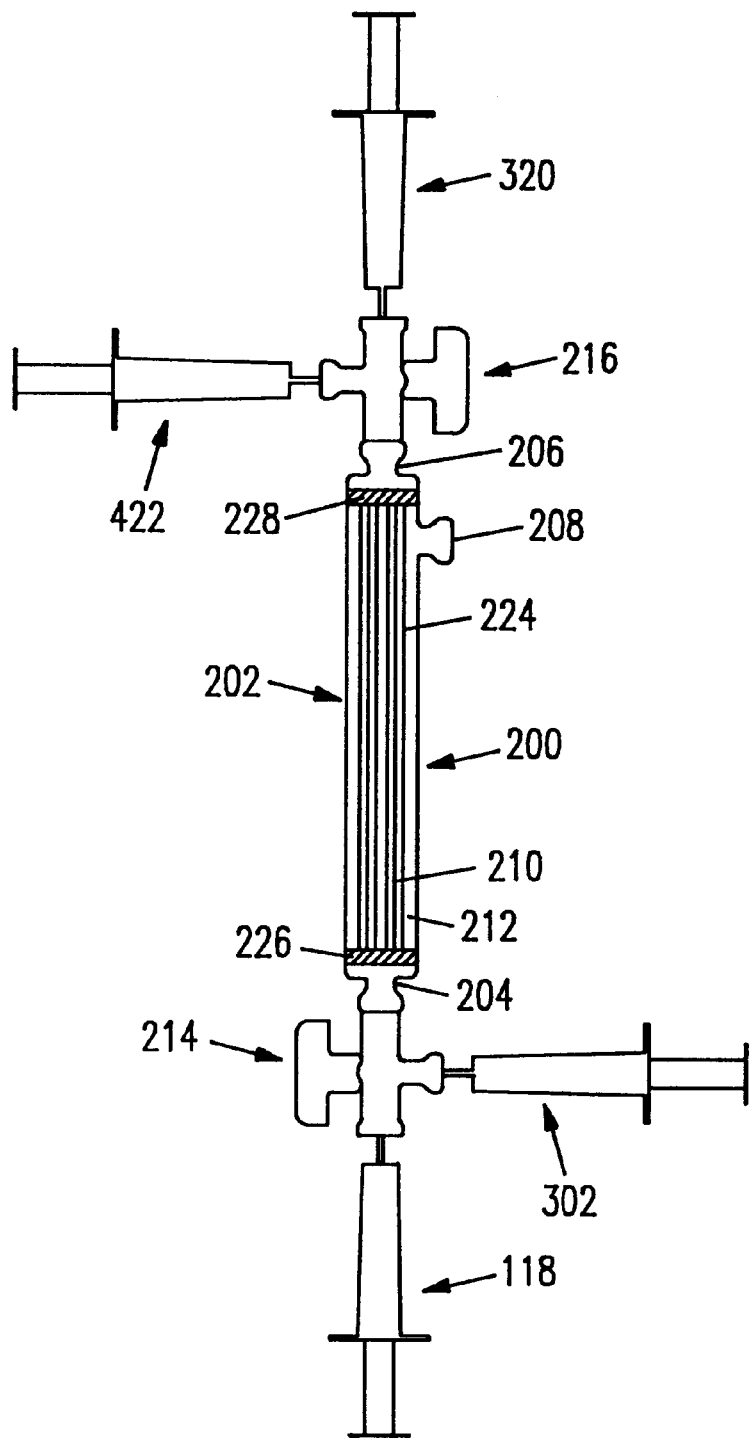
FIG. 4 is a side view of a device similar to that shown in FIGS. 2A and 3 that includes two fluid receptacles.

Another variation of the multi-cycle embodiment is shown in FIG. 4. In this variation, stopcock 216 is a three way stopcock that has a second open position to provide a second flowpath. A second fluid receptacle, illustrated by second receptacle syringe 422 is connected to stopcock 216 so that the second flowpath through stopcock 216 communicates with the interior of second receptacle syringe 422 and with the interior of first receptacle syringe 320. In FIG. 4, a portion of the concentrate stored in first receptacle syringe 320 can be withdrawn by pulling on the plunger of receptacle syringe 422. Such use of two receptacle syringes facilitates using one of the syringes to store concentrate and the other to remove portions of the stored concentrate for use as needed during processing.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention. All literature citations herein are expressly incorporated by reference.

EXAMPLE 1

An exemplary concentration device of this invention was prepared as follows. All of the components used were sterile and were assembled using aseptic technique.

A three-way stopcock (Medex, Inc.) was attached to a female luer lock from a fluid transfer set (Codon Medlon Inc., Cat. No. B310). A 60 cc syringe (Pharmaseal Inc.) used as the fluid delivery syringe was attached to one arm of the stopcock. The second arm was capped with a deadender cap (provided with the stopcock). The third stopcock arm was fitted with a male luer lock to ¼" tubing adapter (Minntech Corp.), which in turn was fitted with a piece of ¼" PVC tubing (about 2 to about 3 cm in length). The ¼" tubing was then connected to one opening of a hemoconcentrator (Minntech Corp.) used as the ultrafiltration unit. The other opening of the hemoconcentrator was also fitted with a similar arrangement to attach a three-way stopcock and a syringe for purge fluid to the opening. However, the syringe used as the purge fluid syringe was a 20 cc syringe (Pharmaseal, Inc.). One outlet of the ultrafiltration unit was capped, and the other was connected to a vacuum source.

The exemplary blood fraction used was plasma from a patient. The plasma was aspirated into a fluid delivery syringe. By adjusting the stopcock, the flow path between the syringe and the hemoconcentrator ultrafiltration unit was opened. A vacuum at about -400 mm Hg was then applied to the outlet of the ultrafiltration unit. Plasma was spontaneously drawn from the fluid delivery syringe into the ultrafiltration unit blood path (the concentrate chamber), and effluent water and entrained constituents were drawn across the ultrafiltration membrane into the filtrate chamber. As the rate of plasma aspiration into the concentrate chamber began to slow substantially, the plunger of the fluid delivery syringe was compressed to force the remaining plasma into the concentrate chamber of the ultrafiltration unit. Once all of the plasma entered the ultrafiltration unit, the vacuum was disconnected. A purge fluid syringe containing physiologic saline was used to infuse purge fluid into the ultrafiltration unit to flush concentrate from the ultrafiltration unit into the fluid delivery syringe. Elapsed time from application of vacuum to completion of concentrate recovery was between four and five minutes using 60 ml of plasma as the blood fraction.

EXAMPLE 2

The procedure of Example 1 was performed on patient plasma. As illustrated in Table 1, the first four samples were plasma diluted with physiologic saline. Sample five was diluted with albumin solution (Baxter Travenol, Springfield, Ill.). The last sample was undiluted. Each of the plasma samples were concentrated to a final volume of 25 ml. Table 1 below illustrates the volume of diluted patient plasma used together with the initial fibrinogen and total protein concentrations and the final concentration of fibrinogen and total protein.

TABLE 1

| Patient Plasma | | | Plasma Concentrate | | |
| --- | --- | --- | --- | --- | --- |
| Volume (ml) | Fibrinogen (g/L) | Total Protein (g/dL) | Volume (ml) | Fibrinogen (g/L) | Total Protein (g/dL) |
| 240 | 49 | 1.3 | 25 | 445 | 11.6 |
| 180 | 104 | 2.5 | 25 | 510 | 12.3 |
| 120 | 148 | 3.8 | 25 | 590 | 15.2 |
| 90 | 212 | 4.9 | 25 | 605 | 14.8 |
| 60 | 95 | 7.6 | 25 | 183 | 15.0 |
| 60 | 275 | 7.3 | 25 | 502 | 14.2 |

As seen from Table 1, the device of this invention concentrates plasma to increase fibrinogen levels and protein levels, as well as the levels of all plasma constituents retained by the membrane. Selected cellular elements, such as platelets and white cells present in the plasma, are similarly retained and concentrated.

What is claimed is:

1. A device for concentrating a blood fraction comprising:
a housing having first and second openings at first and second ends, respectively, and an outlet between said first and second ends, wherein said outlet is adapted to connect to a vacuum source;
a semi-permeable membrane oriented in said housing to define a concentrate chamber that communicates with the first and second openings and a filtrate chamber that communicates with the outlet, said semi-permeable membrane having a molecular weight cut-off suitable for retaining a desired species within said concentrate chamber;
first and second manifolds at the first and second ends, respectively, of said housing;
first and second valves connected to said first and second manifolds, respectively, wherein a first flowpath through each of said valves communicates with the concentrate chamber in a first open position, and said first valve has a second open position wherein the first flowpath is replaced by a second flowpath;
a fluid delivery system connected to said first valve, wherein the first flowpath through said first valve communicates an interior chamber of said fluid delivery system with the concentrate chamber of said housing; and
a purge fluid delivery system connected to said first valve, wherein-the second flowpath through said first valve communicates with an interior chamber of said purge fluid delivery system and with the concentrate chamber of said housing.

2. The device of claim 1 wherein the molecular weight cut-off of said semi-permeable membrane is about 30,000 Daltons.

3. The device of claim 2 wherein said first and second valves are stopcocks.

4. The device of claim 2 wherein said fluid delivery system is selected from the group consisting of a syringe and a fluid transfer bag.

5. The device of claim 2 additionally comprising a first fluid receptacle connected to said second valve, wherein the first flowpath through said second valve communicates with an interior chamber of said fluid receptacle and the concentrate chamber of said housing.

6. The device of claim 5 wherein said fluid receptacle is selected from the group consisting of a syringe and a fluid transfer bag.

7. The device of claim 2 additionally comprising a second fluid receptacle connected to said second valve, wherein the second flowpath through said second valve communicates with an interior chamber of said second fluid receptacle and an interior chamber of said first fluid receptacle.

* * * * *